United States Patent
Chakravarty et al.

(10) Patent No.: US 6,184,226 B1
(45) Date of Patent: *Feb. 6, 2001

(54) QUINAZOLINE DERIVATIVES AS INHIBITORS OF P-38 α

(75) Inventors: Sarvajit Chakravarty, Sunnyvale; John J. Perumattam, Los Altos; George F. Schreiner, Los Altos Hills; David Y. Liu, Palo Alto; John A. Lewicki, Los Gatos, all of CA (US)

(73) Assignee: Scios Inc., Sunnyvale, CA (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/141,916

(22) Filed: Aug. 28, 1998

(51) Int. Cl.$^7$ ............... A01N 55/00; A01K 31/55; C07D 251/00; C07D 401/00; C07D 239/72
(52) U.S. Cl. ............... 514/259; 514/63; 544/180; 544/284; 544/293
(58) Field of Search .......... 514/63, 259; 544/180, 544/284, 293

(56) References Cited

U.S. PATENT DOCUMENTS

| | | | |
|---|---|---|---|
| 4,435,003 | * 3/1984 | Fletcher | 282/27.5 |
| 4,557,998 | 12/1985 | Hollister et al. | |
| 4,695,575 | 9/1987 | Diels et al. | |
| 5,430,148 | 7/1995 | Webber et al. | 544/238 |
| 5,439,895 | 8/1995 | Lee et al. | 514/63 |
| 5,475,001 | 12/1995 | Barker | 514/258 |
| 5,480,883 | 1/1996 | Spada et al. | 514/249 |
| 5,616,582 | 4/1997 | Barker | 514/234.5 |
| 5,650,410 | 7/1997 | Sohda et al. | 514/233.8 |
| 5,658,902 | * 8/1997 | Ahn et al. | 514/234.8 |
| 5,693,652 | 12/1997 | Takase et al. | 514/322 |
| 5,719,157 | 2/1998 | Sohda et al. | 514/259 |
| 5,721,237 | 2/1998 | Myers et al. | 514/259 |
| 5,801,180 | 9/1998 | Takase et al. | 514/259 |

FOREIGN PATENT DOCUMENTS

| | | |
|---|---|---|
| 893984 | 1/1983 | (BE). |
| 3536244 | 4/1986 | (DE). |
| 3501696 | 7/1986 | (DE). |
| 3641872 | 6/1988 | (DE). |
| 3909595 | 9/1990 | (DE). |
| 3921025 | 1/1991 | (DE). |
| 4208254 | 9/1993 | (DE). |
| 4313412 | 10/1994 | (DE). |

(List continued on next page.)

OTHER PUBLICATIONS

Dean et. al., "Cyclic Amidines. Part XXI...", J. Chem. Soc., (C), 1968, Vol. 2, pp. 142–144.*
Brunswick et. al., "Cyclic amidines. Part XXII...", J. Chem. Soc., (C), 1970, Vol. 19, pp. 2641–2647.*
Manhas et. al., "Heterocyclic Compounds XII...", J. Heterocy. Chem., Jun. 1979, Vol. 16 (4), pp. 711–715.*
Lee et. al., "Discovery of Potent Cyclic GMP...", J. Med. Chem., Sep. 1, 1995, Vol. 38 (18), pp. 3547–3557.*
Eyers, P.A. et al. "Conversion of SB 203580–insensitive MAP kinase family members to drug–sensitive forms by a single amino–acid substitution", Chem and Biol (1995) 5:321–328.
Jiang, Y. et al., "Characterization of the structure and function of a new mitogen–activated protein kinase (p38β)" J Biol Chem (1996) 271:17920–17926

(List continued on next page.)

Primary Examiner—Mukund J. Shah
Assistant Examiner—Tamthom N. Truong
(74) Attorney, Agent, or Firm—Morrison & Foerster LLP

(57) ABSTRACT

The invention describes compounds of the formula

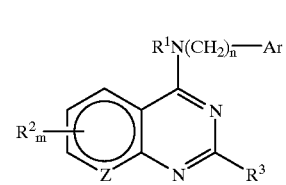

(1)

and the pharmaceutically acceptable salts thereof
and the pharmaceutically acceptable salts thereof wherein each $R^2$ is independently a noninterfering substituent;

m is an integer of 0–4;

Z is CH or N;

$R^1$ is H, alkyl (1–6C) or arylalkyl optionally substituted on the aryl group with 1–3 substituents independently selected from alkyl (1–6C), halo, OR, $NR_2$, SR, —OOCR, —NROCR, RCO, —COOR, —$CONR_2$, —$SO_2NR_2$, CN, $CF_3$, and $NO_2$, wherein each R is independently H or lower alkyl (1–4C);

n is 0, 1 or 2;

Ar is phenyl, pyridyl, indolyl, or pyrimidyl, each optionally substituted with a group selected from the group consisting of optionally substituted alkyl (1–6C), halo, OR, $NR_2$, SR, —OOCR, —NROCR, RCO, —COOR, —$CONR_2$, $SO_2NR_2$, CN, $CF_3$, and $NO_2$, wherein each R is independently H or lower alkyl (1–4C); and $R^3$ is a branched or cyclic alkyl group (5–7C) or is phenyl optionally substituted with 1–2 substituents which substituents are selected from the group consisting of alkyl (1–6C), halo, OR, $NR_2$, SR, —OOCR, —NROCR, RCO, —COOR, —$CONR_2$, —$SO_2NR_2$, CN, $CF_3$, and $NO_2$, wherein each R is independently H or lower alkyl (1–4C) which are useful as antiinflammatories and in treating cardiac disorders.

17 Claims, No Drawings

FOREIGN PATENT DOCUMENTS

| | | |
|---|---|---|
| 4313413 | 10/1994 | (DE). |
| 0567 107 | 10/1993 | (EP). |
| 903349 | 3/1999 | (EP). |
| 2205118 | 11/1988 | (GB). |
| 2295387 | 5/1996 | (GB). |
| 62-165654 | 7/1987 | (JP). |
| 62-165657 | 7/1987 | (JP). |
| 62-168144 | 7/1987 | (JP). |
| 62-166337 | 8/1987 | (JP). |
| 62-168157 | 8/1987 | (JP). |
| 62-293243 | 12/1987 | (JP). |
| 63-041854 | 2/1988 | (JP). |
| 63-307451 | 12/1988 | (JP). |
| 01106055 | 4/1989 | (JP). |
| 01231049 | 9/1989 | (JP). |
| 03240066 | 10/1991 | (JP). |
| 03240067 | 10/1991 | (JP). |
| 73997 | 3/1983 | (WO). |
| WO83/00939 | 3/1983 | (WO). |
| WO83/02920 | 9/1983 | (WO). |
| 164204 | 12/1985 | (WO). |
| 172427 | 2/1986 | (WO). |
| 242324 | 10/1987 | (WO). |
| 271040 | 6/1988 | (WO). |
| 279681 | 8/1988 | (WO). |
| 280224 | 8/1988 | (WO). |
| 283261 | 9/1988 | (WO). |
| 296560 | 12/1988 | (WO). |
| 297661 | 1/1989 | (WO). |
| 326328 | 8/1989 | (WO). |
| 326330 | 8/1989 | (WO). |
| 335319 | 10/1989 | (WO). |
| 372998 | 6/1990 | (WO). |
| 385662 | 9/1990 | (WO). |
| 385663 | 9/1990 | (WO). |
| 407955 | 1/1991 | (WO). |
| 418071 | 3/1991 | (WO). |
| WO91/09853 | 7/1991 | (WO). |
| 450504 | 10/1991 | (WO). |
| 462830 | 12/1991 | (WO). |
| 481802 | 4/1992 | (WO). |
| 485290 | 5/1992 | (WO). |
| WO92107844 | 5/1992 | (WO). |
| WO92/20642 | 11/1992 | (WO). |
| WO92/22552 | 12/1992 | (WO). |
| WO93/23404 | 11/1993 | (WO). |
| 579263 | 1/1994 | (WO). |
| 716855 | 6/1996 | (WO). |
| 742207 | 11/1996 | (WO). |
| WO 96/40143 | 12/1996 | (WO). |
| WO 97 03069 | 1/1997 | (WO). |
| WO 97/26252 | 7/1997 | (WO). |
| WO 98/06715 | 2/1998 | (WO). |
| WO 98/07425 | 2/1998 | (WO). |
| WO 98/27098 | 6/1998 | (WO). |
| WO99/09016 | 2/1999 | (WO). |
| WO 99 32460 | 7/1999 | (WO). |

OTHER PUBLICATIONS

Kumar, S. et al., "Novel homologues of CSBP/p38 MAP kinase: activation, substrate specificity and sensitivity to inhibition by pyridinyl imidazoles", *Biochem Biophys Res Comm* (1997) 235:533–538.

Li, Z. et al. "The primary structure of p38γ: a new member of p38 group of MAP kinases", *Biochem Biophys Res Comm* (1996) 228:334–340.

Stein, B. et al. "p38–2, a novel mitogen–activated protein kinase with distinct properties", *J Biol Chem* (1997) 272:19509–19517.

Wang, X.S., et al. "Molecular cloning and characterization of a novel p38 mitogen–activated protein kinase", *J Biol Chem* (1997) 272:23668–23674.

Wang, Y. et al. "Cardiac muscle cell hypertrophy and apoptosis induced by distinct members of the p38 mitogen–activated protein kinase family", *J Biol Chem* (1998) 273:2161–2168.

* cited by examiner

QUINAZOLINE DERIVATIVES AS INHIBITORS OF P-38 α

FIELD OF THE INVENTION

The invention relates to treating various disorders associated with the activity of the kinase p38-α. More specifically, it concerns compounds that are derivatives of quinazoline as useful in these methods.

BACKGROUND ART

A large number of chronic and acute conditions have been recognized to be associated with perturbation of the inflamniatory response. A large number of cytokines participate in this response, including IL-1, IL-6, IL-8 and TNF. It appears that the activity of these cytokines in the regulation of inflammation rely at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful antiinflammatory agents.

PCT applications WO98/06715, WO98/07425, and WO 96/40143, all of which are incorporated herein by reference, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gramnegative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis.

The above-referenced PCT applications disclose compounds which are p38 kinase inhibitors said to be useful in treating these disease states. These compounds are either imidazoles or are indoles substituted at the 3- or 4-position with a piperazine ring linked through a carboxamide linkage. Additional compounds which are conjugates of piperazines with indoles are described as insecticides in WO97/26252, also incorporated herein by reference.

The compounds of the invention are quinazoline derivatives. Other quinazoline compounds for other uses have been described. U.S. Pat. No. 5,721,237 assigned to Rhone-Poulenc Rorer is directed to methods for selective treatment of cell growth and differentiation characterized by activity of human epidermal growth factor receptor type II using quinazoline substituted only in the 4-position with an aromatic moiety optionally coupled to the quinazoline through a linking moiety. U.S. Pat. No. 4,480,883 describes compounds that exhibit tyrosine kinase inhibition activity wherein the heterocyclic portion of a quinazoline or other fused ring nitrogen-containing aromatic system is substituted only once with an aromatic moiety, again optionally coupled through a linker. U.S. Pat. No. 5,616,582 assigned to Zeneca describes tyrosine kinase inhibitors which are quinazolines linked through an amino group at the 4-position to a substituted or unsubstituted phenyl. These compounds contain no substituents at position 2. U.S. Pat. No. 5,475,001 also assigned to Zeneca describes similar compounds with the same activity. U.S. Pat. No. 5,430,148 assigned to Agouron Pharmaceutical describes antiproliferative substituted quinazolinones and their counterparts wherein the keto group is replaced by a sulfone.

U.S. Pat. No. 5,719,157 to Takeda Chemical Industries describes pharmaceutical compositions for inhibiting bone resorption which include 4-phenyl quinoline derivatives which may further be substituted at the 2-position with an optionally substituted hydrocarbon group or an optionally substituted heterocyclic group.

None of the foregoing patents describes 2, 4-substituted quinazolines which specifically inhibit p38-α.

DISCLOSURE OF THE INVENTION

The invention is directed to compounds useful in treating inflammation generally, including specific conditions such as those described in the Background section above. These novel compounds have been found to inhibit p38 kinase, the α-isoform in particular, and are thus useful in treating diseases mediated by this enzyme. The compounds of the invention are of the formula

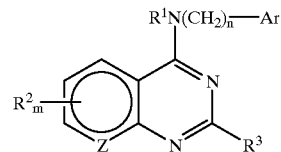

(1)

and the pharmaceutically acceptable salts thereof
  wherein each $R^2$ is independently a noninterfering substituent;
  m is an integer of 0–4;
  Z is CH or N;
  $R^1$ is H, alkyl (1–6C) or arylalkyl optionally substituted on the aryl group with 1–3 substituents independently selected from alkyl (1–6C), halo, OR, $NR_2$, SR, —OOCR, —NROCR, RCO, —COOR, —$CONR_2$, —$SO_2NR_2$, CN, $CF_3$, and $NO_2$, wherein each R is independently H or lower alkyl (1–4C);
  n is 0, 1 or 2;
  Ar is phenyl, pyridyl, indolyl, or pyrimidyl, each optionally substituted with a group selected from the group consisting of optionally substituted alkyl (1–6C), halo, OR, $NR_2$, SR, —OOCR, —NROCR, RCO, —COOR, —$CONR_2$, $SO_2NR_2$, CN, $CF_3$, and $NO_2$, wherein each R is independently H or lower alkyl (1–4C); and
  $R^3$ is a branched or cyclic alkyl group (5–7C) or is phenyl optionally substituted with 1–2 substituents which substituents are selected from the group consisting of alkyl (1–6C), halo, OR, $NR_2$, SR, —OOCR, —NROCR, RCO, —COOR, —$CONR_2$, —$SO_2NR_2$, CN, $CF_3$, and $NO_2$, wherein each R is independently H or lower alkyl (1–4C).

Thus, in one aspect, the invention is directed to compounds of the formula set forth above. In other aspects, the invention is directed to methods to produce these compounds, to pharmaceutical compositions containing them, and to methods of treating inflammation using these compounds. The invention is also directed to treating conditions associated with cardiac failure using the invention compounds.

MODES OF CARRYING OUT THE INVENTION

The compounds of formula (1) are useful in treating conditions which are characterized by overactivity of p38 kinase, and in particular the α-isoform. The compounds are derivatives of quinazoline containing mandatory substituents at the 2- and 4-positions.

With respect to the substituted amino substituent at the 4-position of the quinazoline, the preferred embodiment of $R^1$ is H, but $R^1$ may also be alkyl (1–6C) or arylalkyl where the aryl moiety may be substituted by 1–2 groups, preferably alkyl (1–6C), OR, SR or $NR_2$ wherein R is H or lower alkyl (1–4C). Preferably, $R^1$ is H or alkyl (1–6C).

n may be 0–2, and is preferably 0 or 1 and most preferably 0.

Ar is preferably indolyl, 6-pyrimidyl, or 3- or 4-pyridyl, or is optionally substituted phenyl.

For embodiments wherein Ar is optionally substituted phenyl, preferred substituents include halo, OR, SR, and $NR_2$ wherein R is H or methyl or ethyl. Particularly preferred is 3- or 4-pyridyl, especially 4-pyridyl in unsubstituted form. These substituents may occupy all five positions of the phenyl ring, preferably 1–2 positions, preferably one position.

Any of the aryl moieties, especially the phenyl moieties may also comprise two substituents which, when taken together, form a 5–7 membered carbocyclic or heterocyclic ring.

Thus, preferred embodiments of the substituents at the 4-position of the quinazoline include 2-(4-pyridyl) ethylamino; 4-pyridylamino; 3-pyridylamino; 2-pyridylamino; 4-indolylamino; 5-indolylamino; 3-methoxyanilinyl; 2-(2,5-difluorophenyl)ethylamino-, and the like.

Preferred embodiments of $R^3$, the substituent at the 2-position of the quinazoline comprise a phenyl moiety optionally substituted with 1–2 substituents preferably halo, alkyl (1–6C), OR, $NR_2$, and SR wherein R is as defined above. Preferred substituents at the 2-position of the quinazoline include phenyl, 2-bromophenyl, 2-chlorophenyl, 2-fluorophenyl, 2-methylphenyl, 4-fluorophenyl and the like. Other preferred embodiments of $R^3$ comprise a cyclopentyl or cyclohexyl moiety.

As noted above, $R^2$ is a noninterfering substituent. A "noninterfering substituent" is one whose presence does not substantially destroy the p38-α kinase inhibiting ability of the compound of formula (1) as compared to the case wherein m is 0.

With respect to the nature of the noninterfering substituents, preferably they are selected from $R^4$, halo, $OR^4$, $NR^4_2$, $SR^4$, —$OOCR^4$, —$NR^4OCR^4$, —$COOR^4$, $R^4CO$, —$CONR^4_2$, —$SO_2NR^4_2$, CN, $CF_3$, and $NO_2$, wherein each $R^4$ is independently H, or optionally substituted alkyl (1–6C), or optionally substituted arylalkyl (7–12C) and wherein two $R^2$ taken together may form a fused ring of 5–7 members.

More preferred substituents represented by $R^2$ are those as set forth with regard to the phenyl moieties contained in Ar or $R^3$ as set forth above. m may be 0–4 and is preferably 0–2, and most preferably 1 or 0. When m is 2, two substituents taken together may form a carbocyclic or heterocyclic fused ring of 5–7 atoms. When m is 1, however, preferred substituents are of the formula $R^4$, —$OR^4$, $SR^4$ or $R^4NH$—, especially $R^4NH$—, wherein $R^4$ is defined as above. Particularly preferred are instances wherein $R^4$ is substituted arylalkyl.

The compounds of formula (1) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present on the compound of formula (1), the compound may also be supplied as a salt with a pharmaceutically acceptable cation.

SYNTHESIS OF THE INVENTION COMPOUNDS

The compounds of the invention may be synthesized from the corresponding 4-halo-2-phenyl quinazoline as described in Reaction Scheme 1; which may be obtained from the corresponding 4-hydroxyquinazoline as shown in Reaction Scheme 2. Alternatively, the compounds can be prepared using anthranylamide as a starting material and benzoylating the amino group followed by cyclization to obtain the intermediate 2-phenyl-4-hydroxy quinazoline as shown in Reaction Scheme 3. The compounds of the invention wherein $R^1$ is H can be further derivatized to comprise other embodiments of $R^1$ as shown in Reaction Scheme 4.

Reaction Scheme 1

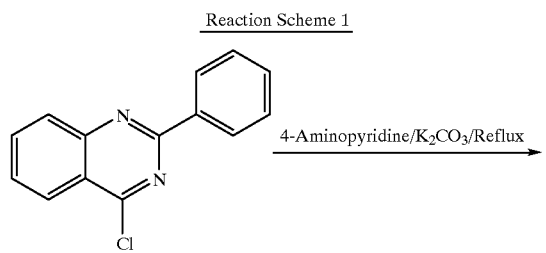

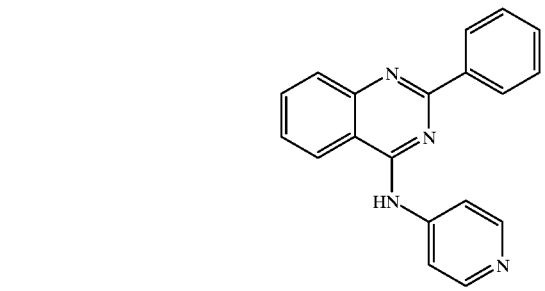

Reaction Scheme 2

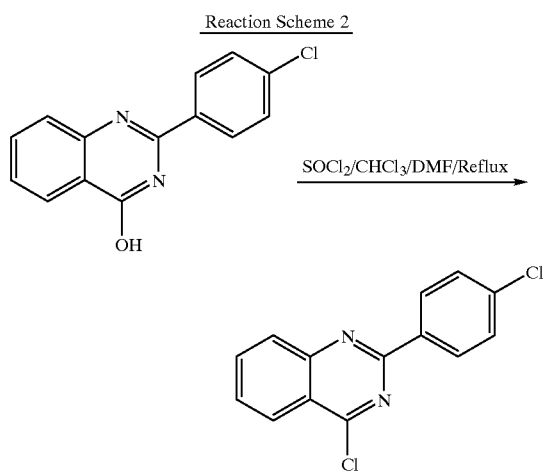

5
-continued
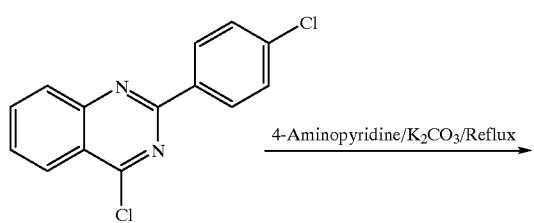
4-Aminopyridine/K₂CO₃/Reflux →
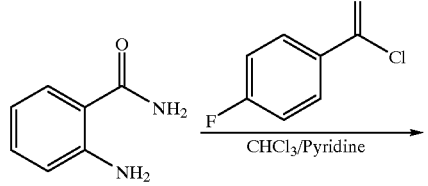
Reaction Scheme 3
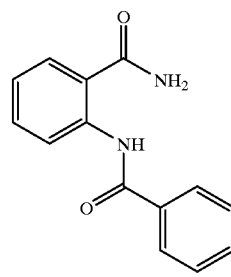
CHCl₃/Pyridine →
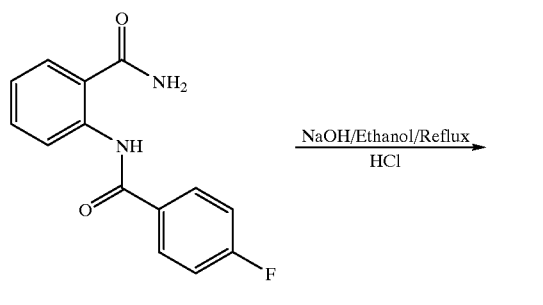
NaOH/Ethanol/Reflux
HCl →
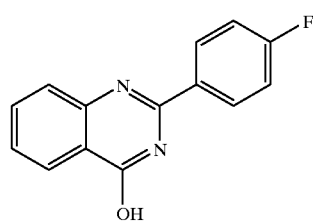
6
-continued
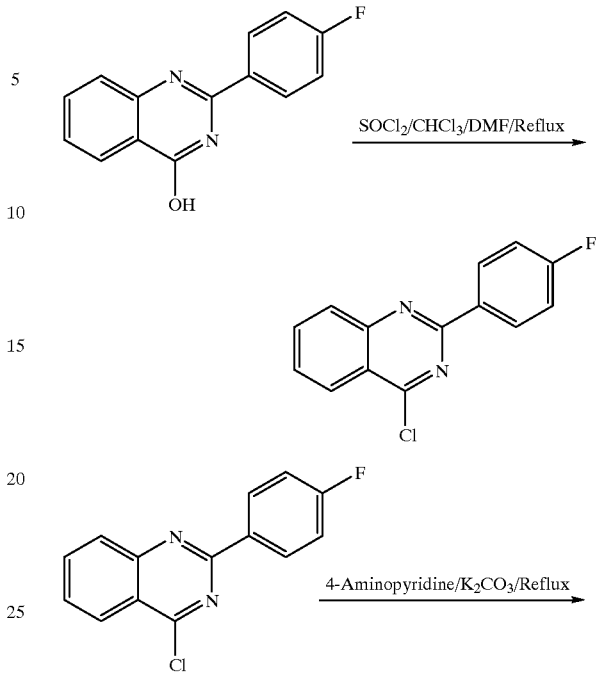
SOCl₂/CHCl₃/DMF/Reflux →
4-Aminopyridine/K₂CO₃/Reflux →
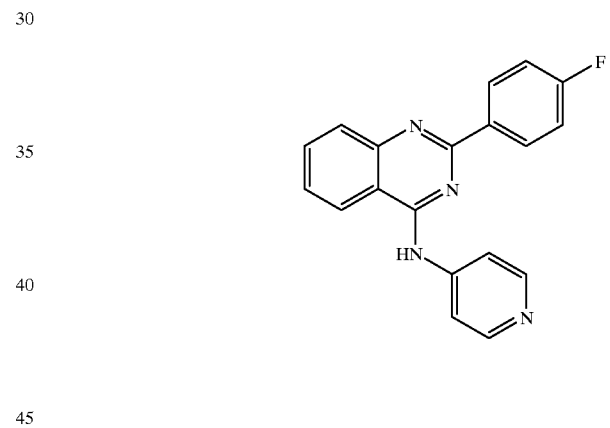
Reaction Scheme 4
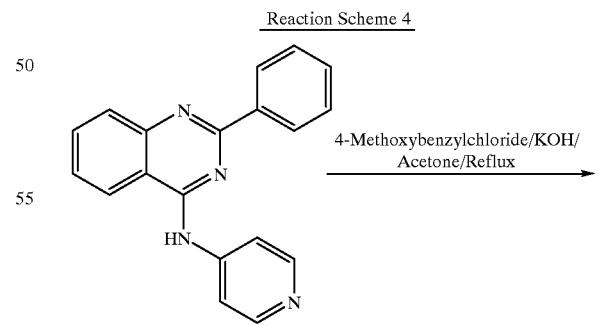
4-Methoxybenzylchloride/KOH/
Acetone/Reflux →

-continued

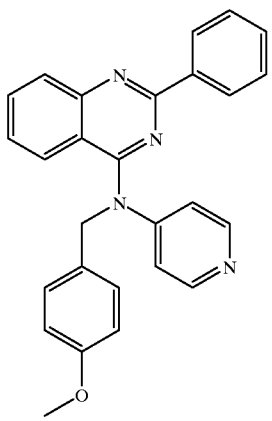

It is seen that Reaction Scheme 1 represents the last step of both Reaction Schemes 2 and 3 and that Reaction Scheme 2 represents the last two steps of Reaction Scheme 3.

Reaction Scheme 4 provides conditions wherein compounds of formula (1) are obtained wherein $R^1$ is other than H.

the reaction scheme. In step a, the starting material is treated with thionyl chloride in the presence of methanol and refluxed for 12 hours. In step b, the appropriate substituted benzoyl chloride is reacted with the product of step a by treating with the appropriately substituted benzoyl chloride in pyridine for 24 hours. In embodiments wherein X (shown illustratively in the ortho-position) is fluoro, 2-fluorobenzoyl chloride is used as a reagent; where X is (for illustration ortho-chloro), 2-chlorobenzoyl chloride is used.

In step c, the ester is converted to the amide by treating in ammonium hydroxide in an aprotic solvent such as dimethyl formamide (DMF) for 24 hours. The product is then cyclized in step d by treatment with 10 N NaOH in ethanol and refluxed for 3 hours.

The resulting cyclized form is then converted to the chloride in step e by treating with thionyl chloride in chloroform in the presence of a catalytic amount of DMF under reflux for 4 hours. Finally, the illustrated 4-pyridylamino compound is obtained in step f by treating with 4-amino pyridine in the presence of potassium carbonate and DMF and refluxed for 2 hours.

In illustrative embodiments of Reaction Scheme 5, $R^2_m$ may be, for example, dimethoxy so that the starting material is 2-amino-4,5-dimethoxy benzoic acid and the product is, for example, 2-(2-chlorophenyl)-4-(4-pyridylamino)-6,7-dimethoxyquinazoline.

Reaction Scheme 5

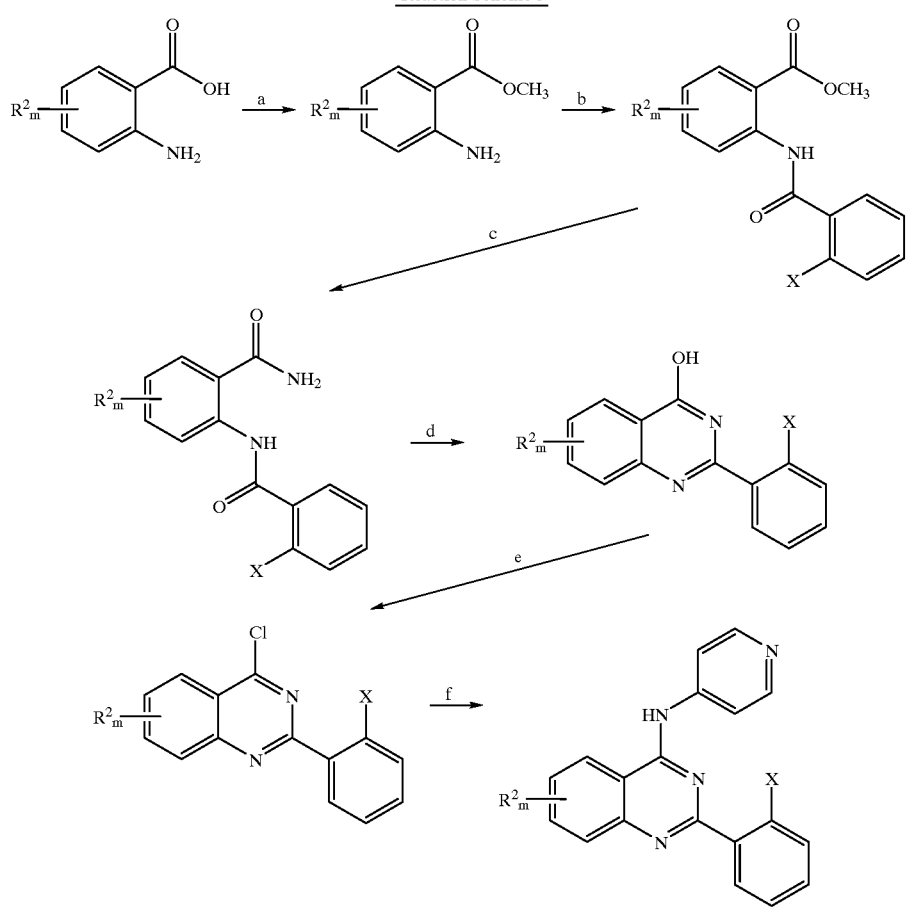

Reaction Scheme 5 shows a modified form of Reaction Scheme 3 which includes substituents $R^2$ in the quinazoline ring of formula (1). The substituents are carried throughout In another illustrative embodiment, $R^2$ is nitro and m is 1; the starting material is thus, for example, 2-amino-5-nitrobenzoic acid and the resulting compound is, for example, 2(2-fluorophenyl)-4-(4-pyridylamino)-5-nitroquinazoline.

In compounds of the invention wherein $R^2$ is nitro, the nitro group may, of course, be reduced to amino and further derivatized as indicated in Reaction Scheme 6.

Reaction Scheme 6

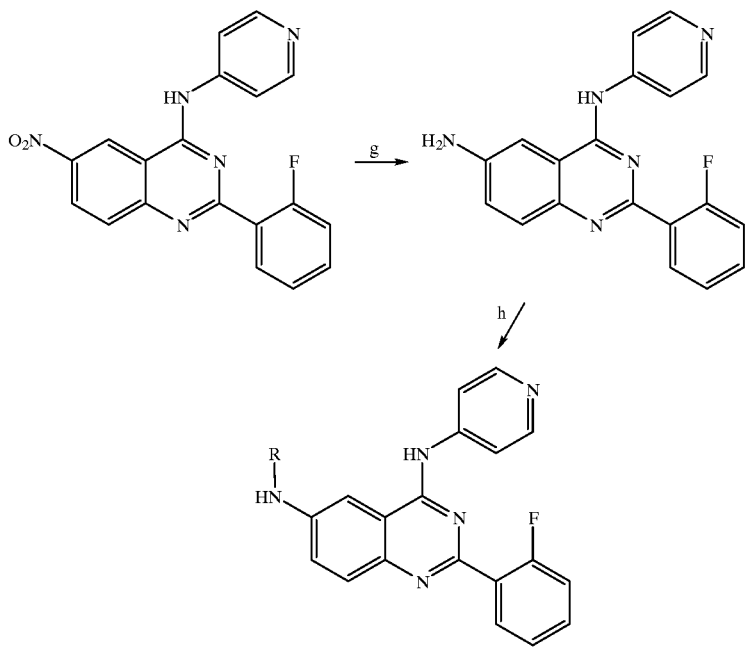

In Reaction Scheme 6, the illustrative product of Reaction Scheme 5 is first reduced in step g by treating with hydrogen and palladium on carbon (10%) in the presence of acetic acid and methanol at atmospheric pressure for 12 hours to obtain the amino compound. The resulting amino compound is either converted to the acyl form (R=acyl) using the appropriate acid chloride in the presence of chloroform and pyridine for four hours, or is converted to the corresponding alkylated amine (R=alkyl) by treating the amine intermediate with the appropriate aldehyde in the presence of ethanol, acetic acid, and sodium triacetoxyborohydride for 4 hours.

While the foregoing exemplary Reaction Schemes are set forth to illustrate the synthetic methods of the invention, it is understood that the substituents shown on the quinazoline ring of the products are generically of the formula (1) as described herein and that the reactants may be substituted accordingly. Variations to accommodate various substituents which represent embodiments of $R^3$ other than the moieties shown in these illustrative examples or as Ar in these illustrative examples may also be used. Similarly, embodiments wherein the substituent at position 4 contains an arylalkyl (i.e., wherein n is 1 or 2) can be used in these schemes. Methods to synthesize the compounds of the invention are, in general, known in the art.

Administration and Use

The compounds of the invention are useful in treating conditions associated with inflammation. Thus, the compounds of formula (1) or their pharmaceutically acceptable salts are used in the manufacture of a medicament for prophylactic or therapeutic treatment of mammals, including humans, in respect of conditions characterized by excessive production of cytokines and/or inappropriate or unregulated cytokine activity on such cells as cardiomyocytes, cardiofibroblasts and macrophages.

The compounds of the invention inhibit the production of cytokines such as TNF, IL-1, IL-6 and IL-8, cytokines that are important proinflammatory constituents in many different disease states and syndromes. Thus, inhibition of these cytokines has benefit in controlling and mitigating many diseases. The compounds of the invention are shown herein to inhibit a member of the MAP kinase family variously called p38 MAPK (or p38), CSBP, or SAPK-2. The activation of this protein has been shown to accompany exacerbation of the diseases in response to stress caused, for example, by treatment with lipopolysaccharides or cytokines such as TNF and IL-1. Inhibition of p38 activity, therefore, is predictive of the ability of a medicament to provide a beneficial effect in treating diseases such as coronary artery disease, congestive heart failure, cardiomyopathy, myocarditis, vasculitis, restenosis, such as occurs following coronary angioplasty, atherosclerosis, rheumatoid arthritis, rheumatoid spondylitis, osteoarthritis, gouty arthritis and other arthritic conditions, multiple sclerosis, acute respiratory distress syndrome (ARDS), asthma, chronic obstructive pulmonary disease (COPD), silicosis, pulmonary sarcosis, sepsis, septic shock, endotoxic shock, toxic shock syndrome, heart and brain failure (stroke) that are characterized by ischemia and reperfusion injury, surgical procedures, such as transplantation procedures and graft rejections, cardiopulmonary bypass, coronary artery bypass graft, CNS injuries, including open and closed head trauma, inflammatory eye conditions such as conjunctivitis and uveitis, acute renal failure, glomerulonephritis, inflammatory bowel diseases, such as Crohn's disease or ulcerative colitis, graft vs. host disease, bone resorption diseases like osteoporosis, type II diabetes, pyresis, psoriasis, cachexia, viral diseases such as those caused by HIV, CMV, and Herpes, and cerebral malaria.

Within the last several years, p38 has been shown to comprise a group of MAP kinases designated p38-α, p38-β, p38-γ and p38-δ. Jiang, Y. et al. *J Biol Chem* (1996) 271:17920–17926 reported characterization of p38-β as a 372-amino acid protein closely related to p38-α. In comparing the activity of p38-α with that of p38-β, the authors state that while both are activated by proinflammatory cytokines and environmental stress, p38-β was preferentially activated by MAP kinase kinase-6 (MKK6) and preferentially activated transcription factor 2, thus suggesting that separate mechanisms for action may be associated with these forms.

Kumar, S. et al. *Biochem Biophys Res Comm* (1997) 235:533–538 and Stein, B. et al. *J Biol Chem* (1997) 272:19509–19517 reported a second isoform of p38-β, p38-β2, containing 364 amino acids with 73% identity to p38-α. All of these reports show evidence that p38-β is activated by proinflammatory cytokines and environmental stress, although the second reported p38-β isoform, p38-β2, appears to be preferentially expressed in the CNS, heart and skeletal muscle compared to the more ubiquitous tissue expression of p38-α. Furthermore, activated transcription factor-2 (ATF-2) was observed to be a better substrate for p38-β2 than for p38-α, thus suggesting that separate mechanisms of action may be associated with these forms. The physiological role of p38-β1 has been called into question by the latter two reports since it cannot be found in human tissue and does not exhibit appreciable kinase activity with the substrates of p38-α.

The identification of p38-γ was reported by Li, Z. et al. *Biochem Biophys Res Comm* (1996) 228:334–340 and of p38-δ by Wang, X., et al., *J Biol Chem* (1997) 272:23668–23674 and by Kumar, S., et al., *Biochem Biophys Res Comm* (1997) 235:533–538. The data suggest that these two p38 isoforms (γ and δ) represent a unique subset of the MAPK family based on their tissue expression patterns, substrate utilization, response to direct and indirect stimuli, and susceptibility to kinase inhibitors.

Various results with regard to response to drugs targeting the p38 family as between p38-α and either the putative p38-β1 or p38-β2 or both were reported by Jiang, Kumar, and Stein cited above as well as by Eyers, P. A. et al. *Chem and Biol* (1995) 5:321–328. An additional paper by Wang, Y. et al. *J Biol Chem* (1998) 273:2161–2168 suggests the significance of such differential effects. As pointed out by Wang, a number of stimuli, such as myocardial infarction, hypertension, valvular diseases, viral myocarditis, and dilated cardiomyopathy lead to an increase in cardiac workload and elevated mechanical stress on cardiomyocytes. These are said to lead to an adaptive hypertrophic response which, if not controlled, has decidedly negative consequences. Wang cites previous studies which have shown that in ischemia reperfusion treated hearts, p38 MAPK activities are elevated in association with hypertrophy and programmed cell death. Wang shows in the cited paper that activation of p38-β activity results in hypertrophy, whereas activation of p38-α activity leads to myocyte apoptosis. Thus, selective inhibition of p38-α activity as compared to p38-β activity will be of benefit in treating conditions associated with cardiac failure. These conditions include congestive heart failure, cardiomyopathy, myocarditis, vasculitis, vascular restenosis, valvular disease, conditions associated with cardiopulmonary bypass, coronary artery bypass, grafts and vascular grafts. Further, to the extent that the α-isoform is toxic in other muscle cell types, α-selective inhibitors would be useful for conditions associated with cachexia attributed to TNF or other conditions such as cancer, infection, or autoimmune disease.

Thus, the invention encompasses the use of compounds which selectively inhibit the activity of the p38-α isoform for treating conditions associated with activation of p38-α, in particular those associated with cardiac hypertrophy, ischemia or other environmental stress such as oxidation injury, hyperosmolarity or other agents or factors that activate p38-α kinase, or cardiac failure, for example, congestive heart failure, cardiomyopathy and myocarditis.

The manner of administration and formulation of the compounds useful in the invention and their related compounds will depend on the nature of the condition, the severity of the condition, the particular subject to be treated, and the judgement of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001–100 mg/kg total body weight, preferably from 0.01–50 mg/kg and more preferably about 0.01 mg/kg–10 mg/kg. The dose regimen will vary, however, depending on the conditions being treated and the judgment of the practitioner.

As implicated above, although the compounds of the invention may be used in humans, they are also available for veterinary use in treating animal subjects.

The following examples are intended to illustrate but not to limit the invention.

EXAMPLE 1

Synthesis of 4-(4-pyridylamino)-2-phenyl quinazoline

This example illustrates Reaction Scheme 1.

A. 4-Chloro-2-phenyl quinazoline, 1 equivalent, was treated with 1 equivalent 4-aminopyridine and 1 equivalent potassium carbonate in dimethylformamide (DMF), under reflux for 4 hours. The reaction mixture was cooled to room temperature and concentrated under vacuum to an oil. This crude material was dissolved in ethyl acetate and chromatographed using hexane:ethyl acetate:methanol 8:2:0.5 to obtain solid product. Electron impact mass spectroscopy (EIMS) gave a molecular ion corresponding to the calculated molecular weight of the title compound.

B. Using the procedure of paragraph A of the example but substituting the starting materials shown in Table 1 below for 4-aminopyridine, the corresponding quinazolines shown in the table were obtained.

TABLE 1

| Substitute for 4-amino pyridine | Product obtained |
| --- | --- |
| 3-amino pyridine | 2-phenyl-4-(3-pyridylamino)-quinazoline |
| 2-amino pyridine | 2-phenyl-4-(2-pyridylamino)-quinazoline |
| 4-aminomethyl pyridine | 2-phenyl-4-(2-(4-pyridyl)methylamino)-quinazoline |
| 3-aminomethyl pyridine | 2-phenyl-4-(2-(3-pyridyl)methylamino)-quinazoline |
| 2-aminomethyl pyridine | 2-phenyl-4-(2-(2-pyridyl)methylamino)-quinazoline |

EXAMPLE 2

Synthesis of 4-(4-pyridylamino)-2-(4-chlorophenyl) quinazoline

This example illustrates Reaction Scheme 2.

A. 4-Chloro-2-(4-chlorophenyl)quinazoline: 4-hydroxy-2-(4-chlorophenyl)quinazoline, 1 equivalent, was suspended in chloroform and treated with 12 equivalents of thionyl chloride in the presence of a catalytic amount of dimethyl formamide, under reflux for 4 hours. After removal of the solvents under reduced pressure, a solid was obtained that was analyzed by thin layer chromatography and EIMS and found to be 4-chloro-2-(4-chlorophenyl)quinazoline.

B. 4-(4-pyridylamino)-2-(4-chlorophenyl)quinazoline: 4-chloro-2-(4-chlorophenyl)quinazoline, 1 equivalent, was treated with 1 equivalent 4-aminopyridine and 1 equivalent potassium carbonate in dimethylformamide (DMF), under reflux for 4 hours, as described in Example 1. The reaction mixture was worked up as in Example 1 and product confirmed by EIMS.

EXAMPLE 3

Synthesis of 4-(4-pyridylamino)-2-(4-fluorophenyl) quinazoline

This example illustrates Reaction Scheme 3.

A. 4-Fluorobenzoyl anthranilamide: Anthranilamide, 1 equivalent, was dissolved in chloroform/pyridine (1:1) and treated with 4-fluorobenzoyl chloride, 1.1 equivalent for one hour at room temperature. The reaction was concentrated under vacuum. The residue was taken up in ethyl acetate and washed with 1 N aqueous sodium carbonate, 10% aqueous hydrochloric acid, saturated sodium chloride solution and dried over anhydrous sodium sulfate. Concentration of the ethyl acetate layer gave a white solid that was found to be homogenous by thin layer chromatography (TLC) and confirmed by EIMS.

B. 4-Hydroxy-2-(4-fluorophenyl)quinazoline: 4-fluorobenzoyl anthranilamide, from paragraph A, 1 equivalent, was dissolved in ethanol and to this was added 10 N aqueous sodium hydroxide, 3.0 equivalents, and the resulting solution heated under reflux for 3 hours. The reaction mixture was cooled to room temperature and concentrated under vacuum. The residue was dissolved in an excess of water and acidified with concentrated hydrochloric acid. A white precipitate forms upon acidification. This precipitate was filtered and washed extensively with water. The solid was then dried under high vacuum in the presence of dessicant. The solid was found to be homogenous by TLC and product confirmed by EIMS.

C. 4-Chloro-2-(4-fluorophenyl)quinazoline: 4-hydroxy-2-(4-fluorophenyl)quinazoline, from paragraph B, 1 equivalent, was suspended in chloroform and treated with 12 equivalents of thionyl chloride in the presence of a catalytic amount of dimethyl formamide, under reflux for 4 hours. After removal of the solvents under reduced pressure a solid was obtained that was analyzed by TLC. EIMS confirmed the desired product.

D. 4-(4-pyridylamino)-2-(4-fluorophenyl)quinazoline: 4-chloro-2-(4-fluorophenyl)quinazoline from paragraph C was reacted as in Example 1 to obtain the title compound.

EXAMPLE 4

Synthesis of 2-Phenyl-4-(3-methoxyanilinyl) quinazoline

4-Chloro-2-phenylquinazoline, 2 equivalents, 3-methoxyanilinyl, 2 equivalents, and potassium carbonate, 2 equivalents, were dissolved in 10 mL isopropanol and refluxed for 2 hours. The precipitated product formed was filtered and washed with water. Recrystallization from methanol provided the product as a white solid that was found to be homogenous by thin layer chromatography (TLC) and confirmed by EIMS.

EXAMPLE 5

Synthesis of 4-(4-Methoxybenzyl-4-pyridylamino)-2-phenyl quinazoline 4-(4-pyridylamino)-2-phenyl quinazoline, 1 equivalent, was dissolved in reagent grade acetone, to this was added 5 equivalents of potassium hydroxide and 1.5 equivalents of 4-methoxybenzyl chloride. The mixture was refluxed under nitrogen for 4 hours. After cooling to room temperature the reaction mixture was concentrated and the residue taken up in ethyl acetate and washed with saturated aqueous sodium chloride and dried over anhydrous sodium sulfate and concentrated to give an oil. This crude material was dissolved in ethyl acetate and chromatographed as in Example 1. EIMS confirmed the product.

EXAMPLE 6

Assay for p38 Kinase Inhibition

The compounds to be tested were solubilized in DMSO and diluted into water to the desired concentrations. The p38 kinase was diluted to 10 μg/ml into a buffer containing 20 mM MOPS, pH 7.0, 25 mM beta-glycerol phosphate, 2 mg/ml gelatin, 0.5 mM EGTA, and 4 mM DTT.

The reaction was carried out by mixing 20 μl test compound with 10 μl of a substrate cocktail containing 500 μg/ml peptide substrate and 0.2 mM ATP (+200 μCi/ml gamma-32P-ATP) in a 4× assay buffer. The reaction was initiated by the addition of 10 μl of p38 kinase. Final assay conditions were 25 mM MOPS, pH 7.0, 26.25 mM beta-glycerol phosphate, 80 mM KCl, 22 mM MgCl$_2$, 3 mM MgSO$_4$, 1 mg/ml gelatin, 0.625 mM EGTA, 1 mM DTT, 125 µg/ml peptide substrate, 50 µM ATP, and 2.5 µg/ml enzyme. After a 40 minute incubation at room temperature, the reaction was stopped by the addition of 10 µl per reaction of 0.25 M phosphoric acid.

A portion of the reaction was spotted onto a disk of P81 phosphocellulose paper, the filters were dried for 2 minutes and then washed 4× in 75 mM H$_3$PO$_4$. The filters were rinsed briefly in 95% ethanol, dried, then placed in scintillation vials with liquid scintillation cocktail.

Alternatively, the substrate is previously biotinylated and the resulting reactions are spotted on SAM$^{2\text{TM}}$ streptavidin filter squares (Promega). The filters are washed 4× in 2M NaCl, 4× in 2M NaCl with 1% phosphoric acid, 2× in water, and briefly in 95% ethanol. The filter squares are dried and placed in scintillation vials with liquid scintillation cocktail.

Counts incorporated are determined on a scintillation counter. Relative enzyme activity is calculated by subtracting background counts (counts measured in the absence of enzyme) from each result, and comparing the resulting counts to those obtained in the absence of inhibitor. IC$_{50}$ values were determined with curve-fitting plots available with common software packages. Approximate IC$_{50}$ values were calculated using formula $$IC_{50}(app) = A \times i/(1-A)$$

where A=fractional activity and i=total inhibitor concentration.

The results, where IC$_{50}$ has been calculated, are as follows:

TABLE 2

| Compound No. | Compound Name | µM IC$_{50}$ vs p38-α |
|---|---|---|
| 16 | 2-phenyl-4-(4-pyridylmethylamino)-quinazoline | 1.2 |
| 7 | 2-phenyl-4-(4-pyridylamino)-quinazoline | 0.457 |
| 8 | 2-(4-fluorophenyl)-(4-pyridylamino)-quinazoline | 0.439 |
| 1 | 2-(2-chlorophenyl)-(4-pyridylamino)-quinazoline | 0.137–(.202) |
| 30 | 2-phenyl-4-(3-methoxyanilinyl)-quinazoline | 0.578 |
| 5 | 2-(2-fluorophenyl)-4-(4-pyridylamino)-quinazoline | 0.114 |
| 4 | 2-(2-bromophenyl)-4-(4-pyridylamino)-quinazoline | 0.285 |
| 3 | 2-(2-methylphenyl)-4-(4-pyridylamino)-quinazoline | 0.345 |
| 40 | 2-(2-fluorophenyl)-4-(4-pyridylamino)-6-amino quinazoline | 0.168 |

The compounds in Table 3 have been assessed in terms of percent inhibition of p38-α activity in the presence of 15 µM concentration. Except as noted, m is 0, Z is CH and R$^1$ is H in all cases.

TABLE 3

| Comp. No. | n | Ar | R$^3$ | % Inhib. |
|---|---|---|---|---|
| 1 | 0 | 4-pyridyl | 2-chlorophenyl | 100 |
| 2 | 0 | 4-pyridyl | 2,6-dichlorophenyl | 85 |
| 3 | 0 | 4-pyridyl | 2-methylphenyl | 99 |
| 4 | 0 | 4-pyridyl | 2-bromophenyl | 99 |
| 5 | 0 | 4-pyridyl | 2-fluorophenyl | 99 |
| 6 | 0 | 4-pyridyl | 2,6-difluorophenyl | 97 |
| 7 | 0 | 4-pyridyl | phenyl | 97–99 |
| 8 | 0 | 4-pyridyl | 4-fluorophenyl | 92 |
| 9 | 0 | 4-pyridyl | 4-methoxyphenyl | 5 |
| 10 | 0 | 4-pyridyl | 3-fluorophenyl | 68 |
| 11* | 0 | 4-pyridyl | phenyl | 69 |
| 12† | 0 | 4-pyridyl | phenyl | 47 |
| 13 | 1 | 4-pyridyl | phenyl | 64 |
| 14 | 1 | 4-pyridyl | 4-chlorophenyl | 51 |
| 15 | 0 | 3-pyridyl | phenyl | 45 |
| 16 | 1 | 2-pyridyl | phenyl | 16 |
| 17 | 1 | 3-pyridyl | phenyl | 54 |
| 18 | 1 | 2-pyridyl | phenyl | 33 |
| 19 | 2 | 2-pyridyl | phenyl | 16 |
| 20 | 0 | 6-pyrimidinyl | phenyl | 97 |
| 21 | 0 | 2-pyrimidinyl | phenyl | 3 |
| 22 | 0 | phenyl | phenyl | 45 |
| 23 | 1 | phenyl | 3-chlorophenyl | 37 |
| 24 | 0 | 3-hydroxyphenyl | phenyl | 19 |
| 25 | 0 | 2-hydroxyphenyl | phenyl | 28 |
| 26 | 0 | 4-hydroxyphenyl | phenyl | 63 |
| 27 | 0 | 4-indolyl | phenyl | 72 |
| 28 | 0 | 5-indolyl | phenyl | 70 |
| 29 | 0 | 4-methoxyphenyl | phenyl | 16 |
| 30 | 0 | 3-methoxyphenyl | phenyl | 95 |
| 31 | 0 | 2-methoxyphenyl | phenyl | 37 |
| 32 | 0 | 4-(2-hydroxyethyl)phenyl | phenyl | 34 |
| 33 | 0 | 3-cyanophenyl | phenyl | 13 |
| 34 | 1 | 2,5-difluorophenyl | phenyl | 63 |
| 35 | 0 | 4-(2-butyl)phenyl | phenyl | 10 |
| 36 | 1 | 4-dimethylaminophenyl | phenyl | 25 |
| 35 | 0 | 4-(2-butyl)phenyl | phenyl | 10 |
| 36 | 1 | 4-dimethylaminophenyl | phenyl | 25 |
| 37 | 0 | 4-pyridyl | cyclophenyl | 58 |

*R$^1$ = 2-propyl
†R$^1$ = 4-methoxyphenyl

Additional compounds were prepared wherein m was 1 or 2. These compounds, wherein R$^1$ is H are shown in Table 4. The percent inhibition was measured at 15 µM compound or at 1 µM compound as indicated.

TABLE 4

| Comp. No. | n | Ar | R$^3$ | R$^2$ | % Inhibition |
|---|---|---|---|---|---|
| 38 | 0 | 4-pyridyl | 2-chlorophenyl | 6,7-dimethoxy | 97 |
| 39 | 0 | 4-pyridyl | 2-fluorophenyl | 6-nitro | 91 |
| 40 | 0 | 4-pyridyl | 2-fluorophenyl | 6-amino | — |
| 41 | 0 | 4-pyridyl | 2-fluorophenyl | 7-amino | 94** |
| 42 | 0 | 4-pyridyl | 2-fluorophenyl | 6-(3-methoxy-benzylamino) | 96** |
| 43 | 0 | 4-pyridyl | 2-fluorophenyl | 6-(4-methoxy-benzylamino) | 96** |
| 44 | 0 | 4-pyridyl | 2-fluorophenyl | 6-(2-isobutyl-amino) | — |
| 45 | 0 | 4-pyridyl | 2-fluorophenyl | 6-(4-methylmer-captobenzyl-amino) | — |
| 46 | 0 | 4-pyridyl | 2-fluorophenyl | m = 0 | 97††** |

**tested at 1 µM
††Z is N

Two of the most effective compounds set forth in Tables 2 and 3 above, compounds 5 and 7, were tested for their specificity for p38 by assessing their ability to inhibit other kinases. These compounds were tested at 50 µM and were soluble at 250 µM in 5% DMSO/95% water. The results are shown in Table 5.

TABLE 5

| Compound | IC$_{50}$ (app)-μM | | | | | | |
|---|---|---|---|---|---|---|---|
| | p38-γ | JNK1 | PKA | PKC | DNA-dep PK (PKD) | cck2 | EGF-R |
| 5 | 227 | 167 | >250 | >100 | 120 | 245 | 4.2 |
| 7 | >300 | >300 | 310 | >500 | 240 | >500 | 34 |

In Table 5, compound 5 is 2-(2-fluorophenyl)-4-(4-pyridylamino)-quinazoline and compound 7 is 2-phenyl-4-(4-pyridylamino)-quinazoline.

As seen in Table 5, these compounds are highly specific for p38-α. In addition, these compounds were assessed with respect to p38-β and gave curve fitted values of IC$_{50}$ as follows: Compound 5: 0.928 μM; Compound 7: 3.65 μM.

What is claimed is:

1. A method to specifically inhibit p-38 α-kinase which method comprises contacting p-38 α-kinase with a compound of the formula:

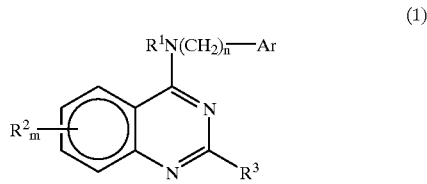

(1)

or the pharmaceutically acceptable salts thereof
wherein each $R^2$ is independently selected from the group consisting of $R^4$, halo, $OR^4$, $NR^4_2$, $SR^4$, —OOCR$^4$, —NR$^4$OCR$^4$, —COOR$^4$, $R^4$CO, —CONR$^4_2$, —SO$_2$NR$^4_2$, CN, CF$_3$, and NO$_2$, wherein each $R^4$ is independently H, or optionally substituted alkyl (1–6C), or optionally substituted arylalkyl (7–12C) and wherein two $R^2$ taken together may form a fused ring of 5–7 members;
m is an integer of 0–4;
$R^1$ is H, alkyl (1–6C) or arylalkyl optionally substituted on the aryl group with 1–3 substituents independently selected from alkyl (1–6C), halo, OR, NR$_2$, SR, —OOCR, —NROCR, RCO, —COOR, —CONR$_2$, —SO$_2$NR$_2$, CN, CF$_3$, and NO$_2$, wherein each R is independently H or lower alkyl (1–4C);
n is 0, 1 or 2;
Ar is phenyl, pyridyl, indolyl, or pyrimidyl, each optionally substituted with a group selected from the group consisting of optionally substituted alkyl (1–6C), halo, OR, NR$_2$, SR, —OOCR, —NROCR, RCO, —COOR, —CONR$_2$, SO$_2$NR$_2$, CN, CF$_3$, and NO$_2$, wherein each R is independently H or lower alkyl (1–4C); and
$R^3$ is a branched (5–7C) or cyclic alkyl group (5C or 7C) or is phenyl optionally substituted with 1–2 substituents which substituents are selected from the group consisting of alkyl (1–6C), halo, SR, —OOCR, —NROCR, RCO, —COOR, —CONR$_2$, —SO$_2$NR$_2$, CN, and CF$_3$, wherein each R is independently H or lower alkyl (1–4C).

2. The method of claim 1 wherein
n is 0; and
$R^3$ is phenyl optionally substituted with 1–2 substituents which are selected from the group consisting of alkyl (1–6C), halo, OR, NR$_2$, SR, —OOCR, —NROCR, RCO, —COOR, —CONR$_2$, —SO$_2$NR$_2$, CN, CF$_3$, and NO$_2$, wherein each R is independently H or lower alkyl (1–4C) or wherein two substituents taken together form a fused ring of 5–7 members.

3. The method of claim 1 wherein $R^3$ is phenyl substituted with 1–2 substituents selected from the group consisting of alkyl (1–6C), OR, NR$_2$, and SR wherein R is H or lower alkyl (1–4C) or where two substituents taken together form a fused ring of 5–7 members.

4. The method of claim 1 wherein Ar is pyridyl, pyrimidyl, indolyl or phenyl optionally substituted with halo, alkyl (1–6C), OR, NR$_2$, or SR wherein R is H or lower alkyl (1–4C).

5. The method of claim 4 wherein Ar is 4-pyridyl, pyrimidyl, indolyl or optionally substituted phenyl.

6. The method of claim 5 wherein Ar is 4-pyridyl or is phenyl substituted with halo, alkyl (1–6C) OR, NR$_2$, or SR wherein R is H or lower alkyl (1–4C).

7. The method of claim 6 wherein Ar is 4-pyridyl or is phenyl substituted with halo or OR wherein R is H or lower alkyl.

8. The method of claim 1 wherein m is 1 and $R^2$ is selected from the group consisting of $R^4$, —OR$^4$, SR$^4$ and R$^4$NH—, wherein each $R^4$ is independently H, or optionally substituted alkyl (1–6C), or optionally substituted arylalkyl (7–12C).

9. The method of claim 8 wherein $R^2$ is $R^4$NH wherein $R^4$ is substituted arylalkyl (7–12C).

10. The method of claim 1 wherein the compound of formula 1 is selected from the group consisting of
2-phenyl-4-(4-pyridylamino)-quinazoline;
2-(2-bromophenyl)-4-(4-pyridylamino)-quinazoline;
2-(2-chlorophenyl)-4-(4-pyridylamino)-quinazoline;
2-(2-fluorophenyl)-4-(4-pyridylamino)-quinazoline;
2-(2-methylphenyl)-4-(4-pyridylamino)-quinazoline;
2-(4-fluorophenyl)-4-(4-pyridylamino)-quinazoline;
2-(3-methoxyanily)-4-(4-pyridylamino)-quinazoline;
2-(2,6-dichlorophenyl)-4-(4-pyridylamino)-quinazoline;
2-(2,6-dibromophenyl)-4-(4-pyridylamino)-quinazoline;
2-(2,6-difluorophenyl)-4-(4-pyridylamino)-quinazoline;
2-(2-fluorophenyl)-4-(4-pyridylamino)-6,7-dimethoxyquinazoline;
2-(4-fluorophenyl)-4-(4-pyridylamino)-6,7-dimethoxyquinazoline;
2-(2-fluorophenyl)-4-(4-pyridylamino)-6-nitroquinazoline;
2-(2-fluorophenyl)-4-(4-pyridylamino-6-aminoquinazoline;
2-(2-fluorophenyl)-4-(4-pyridylamino)-7-aminoquinazoline;
2-(2-fluorophenyl)-4-(4-pyridylamino)-6-(3-methoxybenzylamino)-quinazoline;
2-(2-fluorophenyl)-4-(4-pyridylamino)-6-(4-methoxybenzylamino)-quinazoline;
2-(2-fluorophenyl)-4-(4-pyridylamino)-6-(2-isobutylamino)-quinazoline; and
2-(2-fluorophenyl)-4-(4-pyridylamino)-6-(4-methylmercaptobenzylamino)-quinazoline.

11. The method of claim 1 wherein said compound of formula 1 is contained in a pharmaceutical composition with at least one pharmaceutically acceptable excipient.

12. The method of claim 1 wherein said contacting is performed in a method to treat a condition characterized by a proinflammation response.

13. The method of claim 12 wherein said condition characterized by inflammation is acute respiratory distress syndrome, asthma, chronic obstructive pulmonary disease, uveitis, IBD, acute renal failure, head trauma, or ischemic/reperfusion injury.

14. The method of claim 1 wherein said contacting is performed in a method to treat a heart condition associated with cardiac failure.

15. The method of claim 14 wherein said chronic heart condition is congestive heart failure, cardiomyopathy or myocarditis.

16. A method to prepare the compound defined in claim 1 wherein $R^1$ is not H comprising reacting a compound of the formula

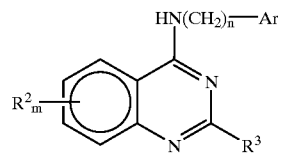

wherein $R^2$, m, $R^3$, n, and Ar are as defined for the compound of formula (1), with a compound of the formula $R^1X$ wherein $R^1$ is as defined for the compound of formula (1) and X is a leaving group, under basic conditions.

17. A method to prepare the compound defined in claim 1 comprising reacting a compound of the formula (2)

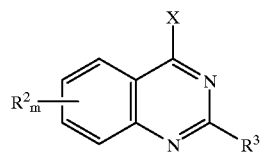

wherein $R^2$, m, and $R^3$, are as defined for said compound of formula (1) and X is a leaving group, with a compound of the formula Ar NH, wherein Ar is as defined for said compound of formula (1).

* * * * *